(12) United States Patent
Wigler et al.

(10) Patent No.: US 6,479,243 B1
(45) Date of Patent: Nov. 12, 2002

(54) METHOD FOR GENERATING LIBRARIES OF ANTIBODY GENES COMPRISING AMPLIFICATION OF DIVERSE ANTIBODY DNAS AND METHODS FOR USING THESE LIBRARIES FOR THE PRODUCTION OF DIVERSE ANTIGEN COMBINING MOLECULES

(75) Inventors: Michael H. Wigler, Lloyd Harbor, NY (US); Joseph A. Sorge, Rancho Santa Fe, CA (US)

(73) Assignee: Stratagene, La Jolla, CA (US)

( * ) Notice: Subject to any disclaimer, the term of this patent is extended or adjusted under 35 U.S.C. 154(b) by 0 days.

(21) Appl. No.: 09/800,229

(22) Filed: Mar. 5, 2001

Related U.S. Application Data

(63) Continuation of application No. 09/439,732, filed on Nov. 12, 1999, which is a continuation of application No. 08/997,195, filed on Dec. 23, 1997, now abandoned, which is a continuation of application No. 08/315,269, filed on Sep. 29, 1994, now Pat. No. 5,780,225, which is a continuation of application No. 07/919,730, filed on Jul. 24, 1992, now Pat. No. 5,284,555, which is a continuation of application No. 07/464,350, filed on Jan. 11, 1990, now abandoned.

(51) Int. Cl.[7] ............................. C12Q 1/68; C12P 19/34
(52) U.S. Cl. ......................................... 435/6; 435/91.2
(58) Field of Search ............................. 435/6, 91.2, 5; 424/204.1

(56) References Cited

U.S. PATENT DOCUMENTS 4,683,195 A   7/1987  Mullis et al. .................. 435/6
5,395,750 A   3/1995  Dillon et al. .................. 435/6

OTHER PUBLICATIONS

Saiki, Randall K. et al., *Science*, 239: 487–491 (1988).
Ohara, Osamu et al., *Proc. Natl. Acad. Sci. USA*, 86: 5673–5677 (1989).
Orlandi, Rosaria et al., *Proc. Natl. Acad. Sci. USA*, 86: 3833–3837 (1989).
Sastry, L. et al., *Proc. Natl. Acad. Sci. USA*, 86: 5728–5732 (1989).
Huse, William D. et al., *Science*, 246: 1275–1281 (1989).
Better, Marc et al., *Science*, 240: 1041–1043 (1988).
Skerra, Arne et al., *Science*, 240: 1038–1041 (1988).
Larrick, J.W. et al., *In Vitro Immunization in Hybridoma Technology.*, pp. 231–246 (1988).
Ward, E. Sally et al., *Nature*, 341: 544–546 (1989).
Moore, Gordon P., *Clin. Chem.*, 35: 1849–1853 (1989).
Larrick, James W. et al., *Biochemical and Biophysical Res. Comm.*, 160(3): 1250–1256 (1989).
Akowitz, Alfred et al., *Gene*, 81: 295–306 (1989).
Belyavsky, A. et al., *Nucleic Acids Research*, 17(8): 2919–2932 (1989).
Larrick, James W. et al., *Methods*, 2(2): 106–110 (1991).
Lee, Roger, *Science*, 237: 1570 (1987).

*Primary Examiner*—Eggerton A. Campbell
(74) *Attorney, Agent, or Firm*—Knobbe, Martens, Olson & Bear, LLP

(57) ABSTRACT

Disclosed is an in vitro process for synthesizing DNA encoding a family of antigen-combining proteins. This process involves obtaining DNA containing genes encoding antigen-combining proteins and then combining these genes with sequence specific primers. These primers can be oligonucleotides homologous to conserved regions of the genes. The genes and primers are then subjected to sequence specific gene amplification.

23 Claims, 5 Drawing Sheets

```
┌─────────────────────────────────────┐
│ CONSTRUCT LIBRARIES OF GENES ENCODING│
│  Ig HEAVY CHAIN AND/ OR LIGHT CHAIN │
│         IN E. COLI VECTOR           │
└─────────────────────────────────────┘
                  │
                  ▼
┌─────────────────────────────────────┐
│   INCREASE DIVERSITY OF LIBRARIES VIA│
│    RANDOM MUTAGENESIS (OPTIONAL)    │
└─────────────────────────────────────┘
                  │
                  ▼
┌─────────────────────────────────────┐
│    TRANSFECT LIBRARIES INTO CULTURED│
│     CELLS, WHERE THEY ARE EXPRESSED │
└─────────────────────────────────────┘
                  │
                  ▼
┌─────────────────────────────────────┐
│         IDENTIFY CULTURED CELLS     │
│   EXPRESSING Ab OF DESIRED SPECIFICITY│
└─────────────────────────────────────┘
                  │
                  ▼
┌─────────────────────────────────────┐
│     ISOLATE GENE(S) ENCODING Ab OF  │
│      DESIRED SPECIFICITY AND EXPRESS│
└─────────────────────────────────────┘
```

*FIG. 1*

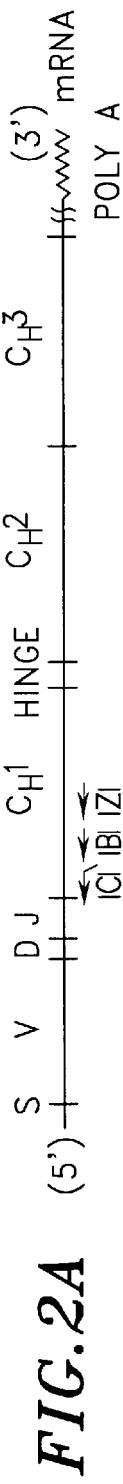

FIG. 4A

```
          >
         AGT   109        118        127
         Ser   CAG TCC TTC CCA AAT GTC TTC
               Gln Ser Phe Pro Asn Val Phe 136            145            154            163            172            181
CCC CTC  GTC TCC TGC    GAG AGC CCC    CTG TCT GAT    AAG AAT CTG    GTG GCC ATG    GGC
Pro Leu  Val Ser Cys    Glu Ser Pro    Leu Ser Asp    Lys Asn Leu    Val Ala MET    Gly 190            199            208            217            226            235
TGC CTA  GCC CGG GAC    TTC CTG CCC    AGC ACC ATT    TCC TTC ACC    TGG AAC TAC    CAG
Cys Leu  Ala Arg Asp    Phe Leu Pro    Ser Thr Ile    Ser Phe Thr    Trp Asn Tyr    Gln 244            253            262            271            280            289
AAC AAC  ACT GAA GTC    ATC CAG GGT    ATC AGA ACC    TTC CCA ACA    CTG AGG ACA    GGG
Asn Asn  Thr Glu Val    Ile Gln Gly    Ile Arg Thr    Phe Pro Thr    Leu Arg Thr    Gly 298            307            316            325            334            343
GGC AAG  TAC CTA GCC    ACC TCG CAG    GTG TTG CTG    TCT CCC AAG    AGC ATC CTT    GAA
Gly Lys  Tyr Leu Ala    Thr Ser Gln    Val Leu Leu    Ser Pro Lys    Ser Ile Leu    Glu 352            361            370            379            388            397
GGT TCA  GAT GAA TAC    CTG GTA TCG    AAA ATC CAC    TAC GGA CCC    AAA AAC AGA    GAT
Gly Ser  Asp Glu Tyr    Leu Val Cys    Lys Ile His    Tyr Gly Pro    Lys Asn Arg    Asp 406            415  > G
CTG CAT  GTG CCC ATT    CCA
Leu His  Val Pro Ile    Pro
```

FIG.4B

METHOD FOR GENERATING LIBRARIES OF ANTIBODY GENES COMPRISING AMPLIFICATION OF DIVERSE ANTIBODY DNAS AND METHODS FOR USING THESE LIBRARIES FOR THE PRODUCTION OF DIVERSE ANTIGEN COMBINING MOLECULES

RELATED APPLICATIONS

This application is a continuation of prior application 09/439,732, filed Nov. 12, 1999, which is a continuation of prior application 08/997,195, filed on Dec. 23, 1999 now abandoned, which is a continuation of prior application 08/315,269, filed on Sep. 29, 1994, now U.S. Pat No. 5,780,225 which is a continuation of prior application 07/919,730, filed on Jul. 24, 1992, now U.S. Pat. No. 5,284,555 which is a continuation of prior application 07/464,350, filed on Jan. 11, 1990 now abandoned.

BACKGROUND OF THE INVENTION

Monoclonal and polyclonal antibodies are useful for a variety of purposes. The precise antigen specificity of antibodies makes them powerful tools that can be used for the detection, quantitation, purification and neutralization of antigens.

Polyclonal antibodies are produced in vivo by immunizing animals, such as rabbits and goats, with antigens, bleeding the animals and isolating polyclonal antibody molecules from the blood. Monoclonal antibodies are produced by hybridoma cells, which are made by fusing, in vitro immortal plasmacytoma cells with antibody producing cells (Kohler, G. and C. Milstein, *Nature* 256:495 (1975)) obtained from animals immunized in vivo with antigen.

Current methods for producing polyclonal and monoclonal antibodies are limited by several factors. First, methods for producing either polyclonal or monoclonal antibodies require an in vivo immunization step. This can be time consuming and require large amounts of antigen. Second, the repertoire of antibodies expressed in vivo is restricted by physiological processes, such as those which mediate self-tolerance that disable autoreactive B cells (Goodnow, C. C., et al., *Nature*, 334:676 (1988); Goodnow, J. W., *Basic and Clinical Immunology*, Ed. 5, Los Altos, Calif., Large Medical Publications (1984); Young, C. R. *Molecular Immunology*, New York, Marcel Dekker (1984)). Third, although antibodies can exist in millions of different forms, each with its own unique binding site for antigen, antibody diversity is restricted by genetic mechanisms for generating antibody diversity (Honjo, T., *Ann. Rev. Immunol.*, 1:499 (1983); Tonegawa, S., *Nature*: 302:575 (1983)). Fourth, not all the antibody molecules which can be generated will be generated in a given animal. As a result, raising high affinity antibodies to a given antigen can be very time consuming and can often fail. Fifth, the production of human antibodies of desired specificity is very problematical.

A method of producing antibodies which avoids the limitations of presently-available methods, such as the requirement' for immunization of an animal and in vivo steps would be very useful particularly if it made it possible to produce a wide range of antibody types than can be made using presently-available techniques and if it made it possible to produce human antibody types.

DISCLOSURE OF THE INVENTION

The present invention relates to a method of producing libraries of genes encoding antigen-combining molecules or antibodies; a method of producing antigen-combining molecules, also reference to as antibodies, which does not require an in vivo procedure, as is required by presently-available methods; a method of obtaining antigen combining molecules (antibodies) of selected or defined specificity which does not require an in vivo procedure; vectors useful in the present method and antibodies produced or obtained by the method.

The present invention relates to an in vitro process for synthesizing DNA encoding families of antigen-combining molecules or proteins. In this process, DNA containing genes encoding antigen-combining molecules is obtained and combined with oligonucleotides which are homologous to regions of the genes which are conserved. Sequence-specific gene amplification is then carried out using the DNA containing genes encoding antigen-combining proteins as template and the homologous oligonucleotides as primers.

This invention also relates to a method of creating diverse libraries of DNAs encoding families of antigen-combining proteins by cloning the product of the in vitro process for synthesizing DNA, described in the preceding paragraph, into an appropriate vector (e.g., a plasmid, viral or retroviral vector).

The subject invention provides an alternative method for the production of antigen-combining molecules, which are useful affinity reagents for the detection and neutralization of antigens and the delivery of molecules to antigenic sites. The claimed method differs from production of polyclonal antibody molecules derived by immunization of live animals and from production of monoclonal antibody molecules through the use of hybridoma cell lines in that it does not require an in vivo immunization step, as do presently available methods. Rather, diverse libraries of genes which encode antigen-combining sites comprising a significant proportion of an animal's repertoire of antibody combining sites are made, as described in detail herein. These genes are expressed in living cells, from which molecules of desired antigenic selectivity can be isolated and purified for various uses.

Antigen-combining molecules are produced by the present method in the following manner, which is described in greater detail below. Initially, a library of antibody genes which includes a set of variable regions encoding a large, diverse and random group of specificities derived from animal or human immunoglobulins is produced by amplifying or cloning diverse genomic fragments or cDNAs of antibody mRNAs found in antibody-producing tissue.

In an optional step, the diversity of the resulting libraries can be increased by means of random mutagenesis. The gene libraries are introduced into cultured host cells, which may be eukaryotic or prokaryotic, in which they are expressed. Genes encoding antibodies of desired antigenic specificity are identified, using a method described herein or known techniques, isolated and expressed in quantities in appropriate host cells, from which the encoded antibody can be purified.

Specifically, a library of genes encoding immunoglobulin heavy chain regions and a library of genes encoding immunoglobulin light chain regions are constructed. This is carried out by obtaining antibody encoding DNA, which is either genomic fragments or cDNAs of antibody mRNAs, amplifying or cloning the fragments or cDNAs; and introducing then into a standard framework antibody gene vector, which is used to introduce the antibody-encoding DNA into cells in which the DNA is expressed. The vector includes a framework gene encoding a protein, such as a gene encoding an antibody heavy chain or an antibody light chain which can be of any origin (human, non-human) and can be derived from any of a number of existing DNAs encoding heavy chain immunoglobulins or light chain immunoglobulins. Such vectors are also a subject of the present invention and are described in greater detail in a subsequent section. Genes from one or both of the libraries are introduced into appropriate host cells, in which the genes are expressed, resulting in production of a wide variety of antigen-combining molecules.

Genes encoding antigen-combining molecules of desired specificity are identified by identifying cells producing antigen-combining molecules which react with a selected antigen and then obtaining the genes of interest. The genes of interest can subsequently be introduced into an appropriate host cell (or can be further modified and then introduced into an appropriate host cell) for further production of antigen-combining molecules, which can be purified and used for the same purposes for which conventionally-produced antibodies are used.

Through use of the method described, it is possible to produce antigen-combining molecules which are of wider diversity than are antibodies available as a result of known methods; novel antigen-combining molecules with a diverse range of specificities and affinities and antigen-combining molecules which are predominantly human in origin. Such antigen-combining molecules are a subject of the present invention and can be used clinically for diagnostic, therapeutic and prophylactic purposes, as well as in research contexts, and for other purposes.

BRIEF DESCRIPTION OF THE DRAWINGS

FIG. 1 is a schematic representation of the method of the present invention by which antigen-combining molecules, or antibodies, are produced.

FIG. 2 is a schematic representation of amplification or cloning of IgM heavy chain variable region DNA from mRNA, using the polymerase chain reaction.

Figure 3:
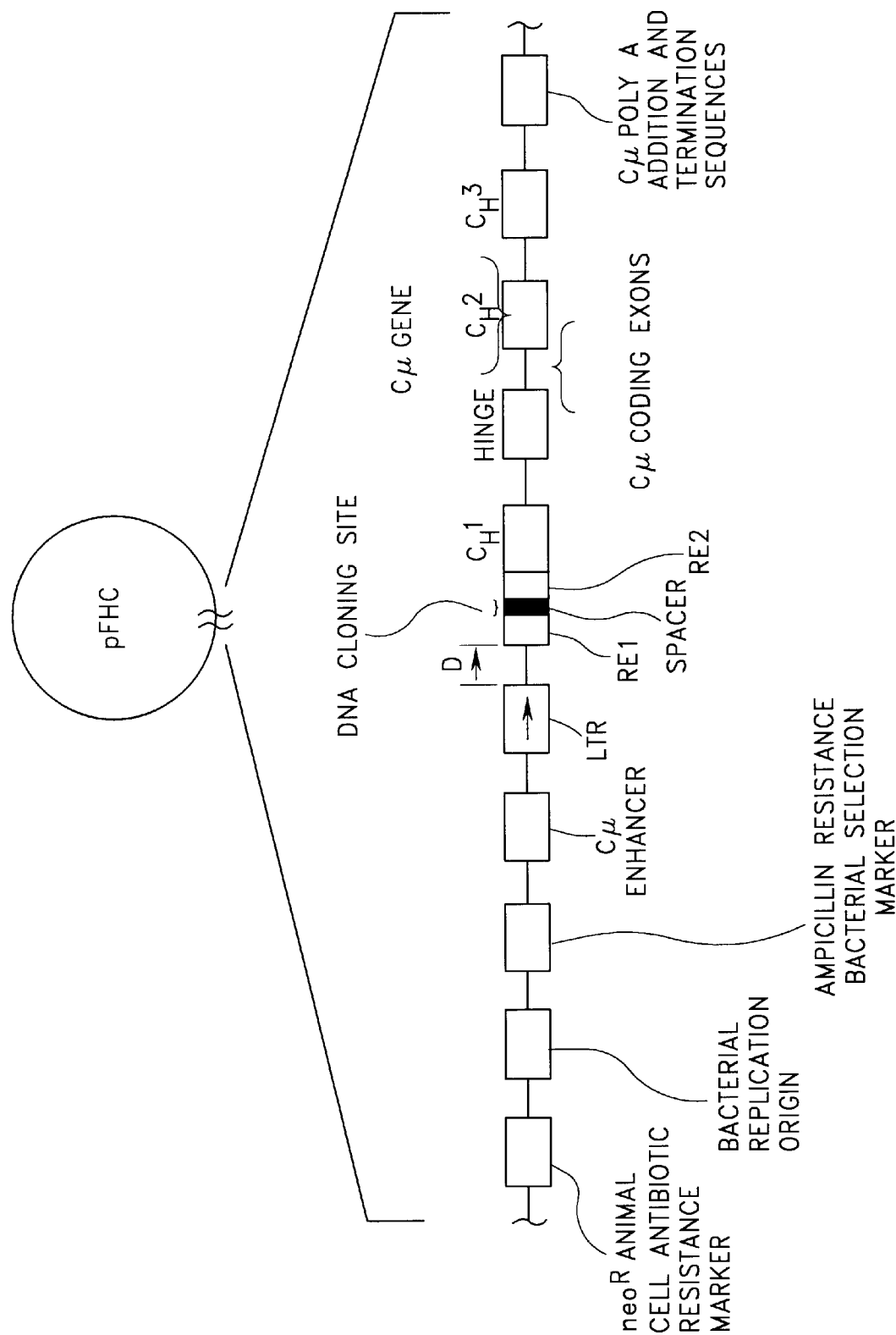

Panel A shows the relevant regions of the poly adenylated mRNA encoding the secreted form of the IgM heavy chain. S denotes the sequences encoding the signal peptide which causes the nascent peptide to cross the plasma membrane. V, D and J together comprise the variable region. $C_H1$, $C_H2$, and $C_H3$ are the three, constant domains of $C\mu$. Hinge encodes the hinge region. C, B and Z are oligonucleotide PCR primers (discussed below).

Panel B shows the reverse transcript DNA product of the mRNA primed by oligonucleotide Z, with the addition of poly-dC by terminal-transferase at the 3' end.

Panel C is a schematic representation of the annealing of primer A to the reverse transcript DNA.

Panel D shows the final double stranded DNA PCR product made utilizing primers A and B.

Panel E shows the product of PCR annealed to primer C.

Panel F is a blowup of Panel E, showing in greater detail the structure of primer C. Primer C consists of two parts: a 3' part complementary to IgM heavy chain mRNA as shown, and a 5' part which contains restriction site RE2 and spacer.

Panel G shows the final double stranded DNA PCR product made utilizing primers A and C and the product of the previous PCR (depicted in D) as template. The S, V, D, J regions are again depicted.

FIG. 3 is a schematic representation of the heavy chain framework vector pFHC. The circular plasmid (above) is depicted linearized (below) and its relevant components are shown: animal cell antibiotic resistance marker; bacterial replication origin; bacterial cell antibiotic resistance marker; $C\mu$ enhancer; LTR containing the viral promoter from the Moloney MLV retrovirus DNA; PCR primer (D); cDNA cloning site containing restriction endonuclease sites, RE1 and RE2, separated by spacer DNA; $C\mu$ exons; and poly A addition and termination sequences derived from the $C\mu$ gene or having the same sequence as the $C\mu$ gene.

Figure 4B:
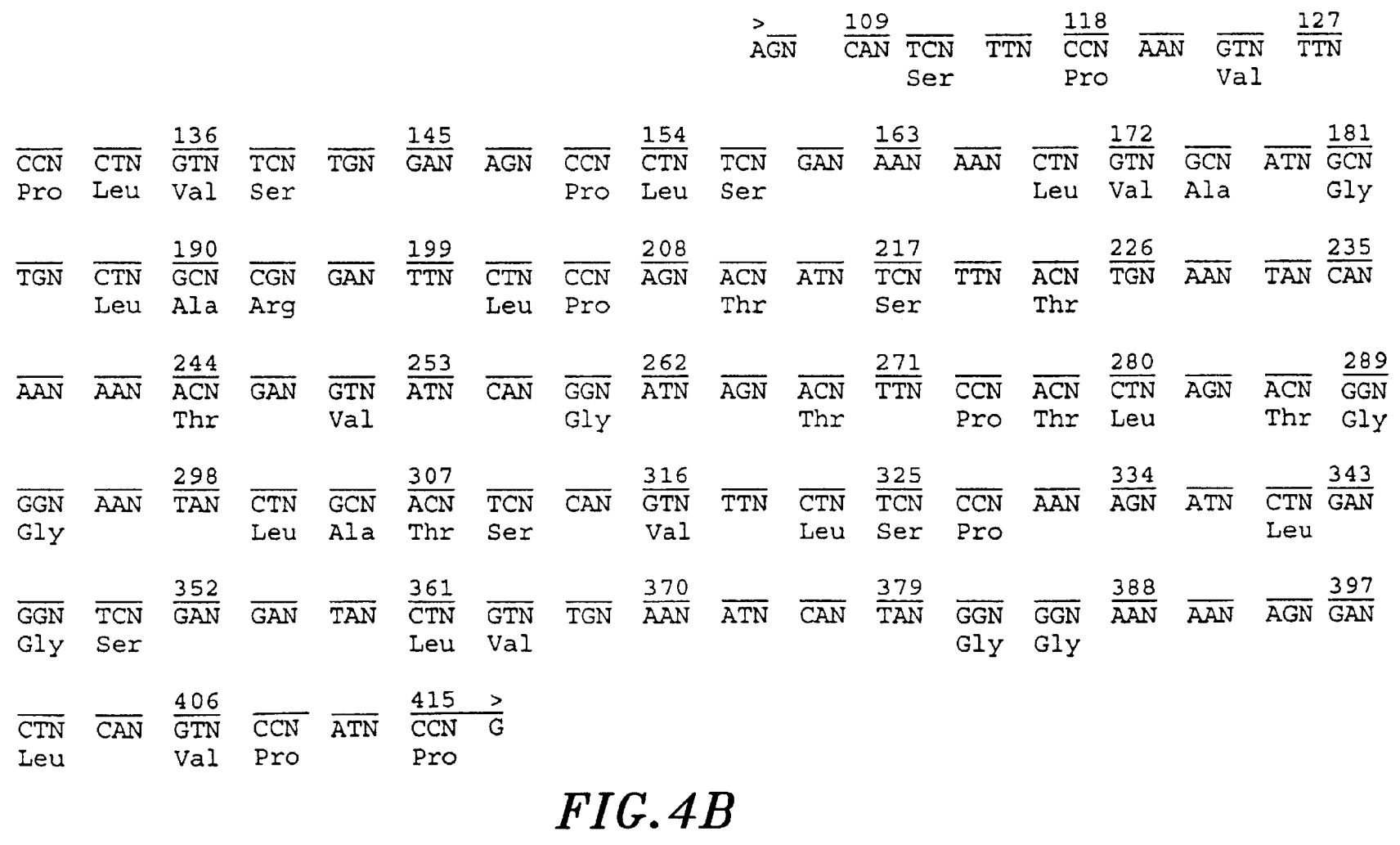

FIG. 4 depicts a nucleotide sequence of the $C_H1$ exon of the $C\mu$ gene, and its encoded amino acid sequence (Panel A). The nucleotide coordinate numbers are listed above the line of nucleotide sequences. Panel B depicts the N-doped sequence, as defined in the text.

DETAILED DESCRIPTION OF THE INVENTION

The present invention provides a method of producing antigen-combining molecules (or antibodies) which does not require an in vivo immunization procedure and which makes it possible to produce antigen-combining molecules with far greater diversity, than is shown by antibodies produced by currently-available techniques.

The present invention relates to a method of producing libraries of genes encoding antigen-combining molecules (antibody proteins) with diverse antigen-combining specificities; a method of producing such antigen-combining molecules, antigen-combining molecules produced by the method and vectors useful in the method. The following is a description of generation of such libraries, of the present method of producing antigen-combining molecules of selected specificity and of vectors useful in producing antigen-combining molecules of the present invention.

As described below, the process makes use of techniques which are known to those of skill in the art and can be applied as described herein to produce and identify antigen-combining molecules of desired antigenic specificity: the polymerase chain reaction (PCR), to amplify and clone diverse cDNAs encoding antibody mRNAs found in antibody-producing tissue; mutagenesis protocols to further increase the diversity of these cDNAs; gene transfer protocols to introduce antibody genes into cultured (prokaryotic and eukaryotic cells for the purpose of expressing them; and screening protocols to detect genes encoding antibodies of the desired antigenic specificity. A general outline of the present method is represented in FIG. 1.

Construction of Library of Genes Encoding Antigen-Combining Molecules

A key step in the production of antigen-combining molecules by the present method is the construction of a "library" of antibody genes which include "variable" regions encoding a large, diverse, but random set of specificities. The library can be of human or non-human origin and is constructed as follows:

Initially, genomic DNA encoding antibodies or cDNAs of antibody mRNA (referred to as antibody-encoding DNA) is obtained. This DNA can be obtained from any source of antibody-producing cells, such as spleen cells, peripheral blood cells, lymph nodes, inflammatory tissue cells and bone marrow cells. It can also be obtained from a genomic library or cDNA library of B cells. The antibody-producing cells can be of human or non-human origin; genomic DNA or mRNA can be obtained directly from the tissue (i.e., without previous treatment to remove cells which do not produce antibody) or can be obtained after the tissue has been treated to increase concentration of antibody-producing cells or to select a particular type(s) of antibody-producing cells (i.e., treated to enrich the content of antibody-producing cells). Antibody-producing cells can be stimulated by an agent which stimulates antibody mRNA production (e.g., lipopolysaccharide) before DNA is obtained.

Antibody-encoding DNA is amplified and cloned using a known technique, such as the PCR using appropriately-selected primers, in order to produce sufficient quantities of the DNA and to modify the DNA in such a manner (e.g., by addition of appropriate restriction sites) that it can be introduced as an insert into an E. coli cloning vector. This cloning vector can serve as the expression vector or the inserts can later be introduced into an expression vector, such as the framework antibody gene vector described below. Amplified and cloned DNA can be further diversified, using mutagenesis, such as PCR, in order to produce a greater diversity or wider repertoire of antigen-binding molecules, as well as novel antigen-binding molecules.

Cloned antibody-encoding DNA is introduced into an expression vector, such as the framework antibody gene vector of the present invention, which can be a plasmid, viral or retroviral vector. Cloned antibody-encoding DNA is inserted into the vector in such a manner that the cloned DNA will be expressed as protein in appropriate host cells. It is essential that the expression vector used make it possible for the DNA insert to be expressed as a protein in the host cell. One expression vector useful in the present method is referred to as the framework antibody gene vector. Vectors useful in the present method contain antibody constant region or portions thereof in such a manner that when amplified DNA is inserted, the vector expresses a chimeric gene product comprising a variable region and a constant region in proper register. The two regions present in the chimeric gene product can be from the same type of immunoglobulin molecule or from two different types of immunoglobulin molecules.

These libraries of antibody-encoding genes are then expressed in cultured cells, which can be eukaryotic or prokaryotic. The libraries can be introduced into host cells separately or together. Introduction of the antibody-encoding DNA in vitro into host cells (by infection, transformation or transfection) is carried out using known techniques, such as electroporation, protoplast fusion or calcium phosphate co-precipitation. If only one library is introduced into a host cell, the host cell will generally be one which makes the other antibody chain, thus making it possible to produce complete/functional antigen-binding molecules. For example, if a heavy chain library produced by the present method is introduced into host cells, the host cells will generally be cultured cells, such as myeloma cells or E. coli, which naturally produce the other (i.e., light) chain of the immunoglobulin or are engineered to do so. Alternatively, both libraries can be introduced into appropriate host cells, either simultaneously or sequentially.

Host cells in which the antibody-encoding DNA is expressed can be eukaryotic or prokaryotic. They can be immortalized cultured animal cells, such as a myeloma cell line which has been shown to efficiently express and secrete introduced immunoglobulin genes (Morrison, S. L., et al., Ann. N.Y. Acad. Sci., 502:187 (1987); Kohler. G. and C. Milstein, Eur. J. Immunol., 6:511 (1976); Oi, V. T. et al. Immunoglobulin Gene Expression in Transformed Lymphoid Cell, 80:825 (1983); Davis, A. C. and M. J. Shulman, Immunol. Today, 10:119 (1989)). One host cell which can be used to express the antibody-encoding DNA is the J558L cell line or the SP2/0 cell line.

Cells expressing antigen-combining molecules with a desired specificity for a given antigen can then be selected by a variety of means, such as testing for reactivity with a selected antigen using nitrocellulose layering. The antibodies identified thereby can be of human origin, nonhuman origin or a combination of both. That is, all or some of the components (e.g., heavy chain, light chain, variable regions, constant regions) can be encoded by DNA of human or nonhuman origin, which, when expressed produces the encoded chimeric protein which, in turn, may be human, nonhuman or a combination of both. In such antigen-combining molecules, all or some of the regions (e.g. heavy and light chain variable and constant regions) are referred to as being of human origin or of nonhuman origin, based on the source of the DNA encoding the antigen-combining molecule region in question. For example, in the case in which DNA encoding mouse heavy chain variable region is expressed in host cells, the resulting antigen-combining molecule has a heavy chain variable region of mouse origin. Antibodies produced may be used for such purposes as drug delivery, tumor imaging and other therapeutic, diagnostic and prophylactic uses.

Once antibodies of a desired binding specificity are obtained, their genes may be isolated and further mutagenized to create additional antigen combining diversity or antibodies of higher affinity for antigen.

Construction of Immunoglobulin Heavy Chain Gene Library and Production of Encoded Antigen-Binding Molecules The following is a detailed description of a specific experimental protocol which embodies the concepts described above. Although the following is a description of one particular embodiment, the same procedures can be used to produce libraries in which the immunoglobulin and the heavy chain class are different or in which light chain genes are amplified and cloned. The present invention is not a intended to be limited to this example. In the embodiment presented below, a diverse heavy chain gene library is constructed. Using the principles described in relation to the heavy chain gene library, a diverse light chain gene library is also constructed. These are co-expressed in an immortal tumor cell capable of producing antibodies, such as plasmacytoma cells or myeloma cells. Cells expressing antibody reactive to antigen are identified by a nitrocellulose filter overlay and antibody is prepared from cells identified as expressing it. As described in a subsequent section, there are alternative methods of library construction, other expression systems which can be used, and alternative selection systems for identifying antibody-producing cells or viruses.

Step 1 in this specific protocol is construction of libraries of genes in E. coli which encode immunoglobulin heavy chains. This is followed by the use of random mutagenesis to increase the diversity of the library, which is an optional procedure. Step 2 is introduction of the library, by transfection, into myeloma cells. Step 3 is identification of myeloma cells expressing antibody with the desired specificity, using the nitrocellulose filter overlay technique or techniques known to those of skill in the art. Step 4 is isolation of the gene(s) encoding the antibody with the desired specificity and their expression in appropriate host cells, to produce antigen-combining fragments useful for a variety of purposes.

Construction

One key step in construction of the library of cDNAs encoding the variable region of mouse heavy chain genes is construction of an E. coli plasmid vector, designated pFHC.

pFHC contains a "framework" gene, which can be any antibody heavy chain and serves as a site into which the amplified cloned gene product (genomic DNA or cDNA of antibody mRNAs) is introduced pFHC is useful as a vector for this purpose because it contains RE1 and RE2 cloning sites. Other vectors which include a framework gene and other cloning sites can be used for this purpose as well. The framework gene includes a transcriptional promoter (e.g., a powerful promoter, such as a Moloney LTR (Mulligan, R. C. *In Experimental Manipulation of Gene Expression*, New York Academic Press, p. 155 (1983)) and a $C\mu$ chain transcriptional enhancer to increase the level of transcriptions from the promoter (Gillies, S. D., et al., *Cell*, 33:717 (1983), a cloning site containing RE1 and RE2; part of the $C\mu$ heavy chain gene encoding secreted protein; and poly A addition and termination sequences (FIG. 3). The framework antibody gene vector of the present invention (pFHC) also includes a selectable marker (e.g., an antibiotic resistance gene such as the neomycin resistance gene, neo$^R$) for animal cells; sequences for bacterial replication (ori); and a selectable marker (e.g., the ampicillin resistance gene, Amp$^R$) for bacterial cells- The framework gene can be of any origin (human, non-human), and can derive from any one of a number of existing DNAs encoding heavy chain immunoglobulins (Tucker, P. W. et el., *Science*, 206:1299 (1979); Honjo T., et al., *Cell*, 18:559 (1979); Bothwell, A. L. M. et al., *Cell*, 24:625 (1981); Liu, A. Y. et al., *Gene*, 54:33 (1987); Kawakami T., et al., *Nuc Acids. Res.*, 8:3933 (1980)). In this embodiment, the vector retains the introns between the $C_H1$, hinge, $C_H2$ and $C_H3$ exons. The "variable region" of the gene, which includes the V, D and J regions of the antibody heavy chain and which encodes the antigen binding site, is deleted and replaced with two consecutive restriction endonuclease cloning sites, RE1 and RE2. The restriction endonuclease site RE1 occurs just 3' to the LTR promoter and the restriction endonuclease site RE2 occurs within the constant region just 3' to the J region (see FIG. 3).

Another key step in the production of antigen-combining molecules in this embodiment of the present invention is construction in an *E. coli* vector of a library of cDNAs encoding the variable region of mouse immunoglobulin genes. In, this embodiment, the pFHC vector, which includes cloning sites designated RE1 and RE2, is used for cloning heavy chain variable regions, although any cloning vector with cloning sites having the same or similar characteristics (described below) can be used. Similarly, a light chain vector can be designed, using the above described procedures and procedures known to a person of ordinary skill in the art.

In this embodiment, non-immune mouse spleens are used as the starting material. mRNA is prepared directly from the spleen or from spleen processed in such a manner that it is enriched for resting B cells. Enrichment of tissue results in a more uniform representation of antibody diversity in the starting materials.

Lymphocytes can be purified from spleen using ficoll gradients (Boyum, A., *Scand. J. of Clinical Invest.*, 21:77 (1968)). B cells are separated from other cells (e.g., T cells) by panning with anti-IgM coated dishes (Wysocki, L. G. and V. L. Sato, *Proc. Natl. Acad. Sci.*, 75:2844 (1978)). Because activated cells express the IL-2 receptor but resting B cells do not, resting B cells can be separated yet further from activated cells by panning. Further purification by size fractionation on a Cell Sorter results in a fairly homogeneous population of resting B cells.

Poly A+ mRNA from total mouse spleen is prepared according to published methods (Sambrook, J., et al., *Molecular Cloning: A Laboratory Manual*, 2d Ed., Cold Spring Harbor Laboratory Press, Cold Spring Harbor, N.Y. (1989)). Production of antibody mRNA can first be stimulated by lipopolysaccharide (LPS) (Andersson, J. A. et al. *J. Exp. Med.*, 145:1511 (1977)). First strand cDNA is prepared to this mRNA population-using as primer an oligonucleotide, Z, which is complementary to $C\mu$ in the $C_H1$ region 3' to J. This primer is designated Z in FIG. 2. First strand cDNA is then elongated by the terminal transferase reaction with dCTP to form a poly dC tail (Sambrook, J., et al., *Molecular Cloning: A Laboratory Manual*, 2d Ed., Cold Spring Harbor Laboratory Press, Cold Spring Harbor, N.Y. (1989)).

This DNA product is then used as template in a polymerase chain reaction (PCR) to amplify cDNAs encoding antibody variable regions (Saiki, R. K., et al., *Science*, 239:487 (1988); Ohara, O., et al., *Proc. Natl. Acad. Sci. USA*, 86:5673 (1989)). Initially, PCR is carried out with two primers: primer A and primer B, as represented in FIG. 2. Primer A contains the RE1 site at its 5' end, followed by poly dG. Primer B is complementary to the constant ($C_H1$) region of the $C\mu$ gene, 3' to the J region and 5' to primer Z (see FIG. 2). Primer B is complementary to all $C\mu$ genes, which encode the heavy chain of molecules of the IgM class, the Ig class expressed by all B cell clones prior to class switching (Schimizu, A. and T. Honjo, *Cell*, 36:801–803 (1984)) and present in resting B cells. The resultant PCR product includes a significant proportion of cDNAs encompassing the various $V_H$ regions expressed as IgM in the mouse. (The use of other primers complementary to the cDNA genes encoding the constant regions of other immunoglobulin heavy chains can be used in parallel reactions to obtain the variable regions expressed on these molecules, but for simplicity these are not described).

Next, the product of the first PCR procedure is used again for PCR with primer A and primer C. Primer C, like primer B, is complementary to the $C\mu$ gene 3' to J and just 5' to primer B (see FIG. 2). Primer C contains the RE2 site at its 5' end. The RE2 sequence is chosen in such a manner that when it is incorporated into the framework vector, no alteration of coding sequence of the $C\mu$ chain occurs (See FIGS. 2 and 3). This method of amplifying $C\mu$ cDNAs, referred to as unidirectional nested PCR, incorporates the idea of nested primers for cloning a gene when the nucleotide sequence of only one region of the gene is known (Ohara, O., et al., *Proc. Natl. Acad. Sci. USA*, 86:5673 (1989)). The PCR product is then cleaved with restriction enzymes RE1 and RE2 and cloned into the RE1 and RE2 sites of the pFHC vector (described below). The sequence of primers and of RE1 and RE2 sites are selected so that when the PCR product is cloned into these sites, the sites are recreated and the cloned antibody gene fragments are brought back into the proper frame with respect to the framework immunoglobulin gene present in pFHC. This results in creation of a $C\mu$ minigene which lacks the intron normally present between J and the $C_H1$ region of $C\mu$ (See FIG. 3). These procedures result in proclamation of the heavy chain library used to produce antigen-binding molecules of the present invention, as described further below.

Optionally, diversity of the heavy chain variable region is increased by random mutagenesis, using techniques known to those of skill in the art.

For example, the library produced as described above is amplified again, using PCR under conditions of limiting nucleotide concentration. Such conditions are known to increase the infidelity of the polymerization and result in production of mutant products. Primers useful for this reaction are Primers C and D, as represented in FIGS. 2 and 3. Primer D derives from pFHC just 5' to RE1. The PCR product, after cleavage with RE1 and RE2, is recloned into the framework vector pFHC. To the extent that mutation affects codons of the antigen binding region, this procedure increases the diversity of the binding domains. For example, if the starter library has a complexity of $10^6$ elements, and an average of one mutation is introduced per complementarity determining region, and it is assumed that the complementarity determining region is 40 amino acids in size and that any of six amino acid substitutions can occur at a mutated codon, the diversity of the library can be increased by a factor of about 40×6, or 240, for single amino acid changes and 240×240, or about $6 \times 10^4$, for double amino acid changes, yielding a final diversity of approximately $10^{11}$. This is considered to be in the, range of the diversity of antibodies which animals produce (Tonegawa, S., *Nature* 302:575 (1983)). Even greater diversity can be generated by the random combination of H and L chains, the result of co-expression in host cells (see below). It is, thus, theoretically possible to generate a more diverse antibody library in vitro than can be generated in vivo. This library of genes is called the "high diversity" heavy chain library. It may be propagated indefinitely in *E. coli*. A high diversity light chain library can be prepared similarly.

The framework vector for the light chain library, designated pFLC, includes components similar to those in the vector for the heavy chain library: the enhancer, promoter, a bacterial selectable marker, an animal selectable marker, bacterial origin of replication and light chain exons encoding the constant regions. For pFLC the animal selectable marker should differ from the animal selectable in pFHC. For example, if pFHC contains $neo^R$, pFLC can contain Eco gpt.

A light chain library, which contains diverse light chain fragments, is prepared as described above for construction of the heavy chain library. In constructing the light chain library, the primers used are different from those described above for heavy chain library construction. In this instance, the primers are complementary to light chain mRNA encoding constant regions. The framework vector contains the light chain constant region exons.

Introduction of the Library of Immunoglobulin Chain Genes into Immortalized Animal Cells The library of immunoglobulin chain genes produced as described is subsequently introduced into a line of immortalized cultured animal cells, referred to as the host cells, in which the genes in the library are expressed. Particularly useful for this purpose are plasmacytoma cell lines or myeloma cell lines which have been shown to efficiently express and secrete introduced immunoglobulin genes (Morrison, S. L. et al., *Ann. N.Y. Acad. Sci.*, 507:187 (1987); Kohler, G. and C. Milstein, *Eur. J. Immunol.*, 6:511 (1976); Galfre and C. Milstein, *Methods Enzymol.*, 73:3 (1981): Davis, A. C. and M. J. Shulman, *Immunol. Today*, 10:119 (1989)). For example, the J558L cell line can be, cotransfected using electroporation or protoplast fusion (Morrison, S. L., et al., *Ann. N.Y. Acad. Sci.*, 522:1187 (1987)) and transfected cells selected on the basis of auxotrophic markers present on light and heavy chain libraries.

As a result of cotransformation and selection for markers on both light chain and heavy chain vectors, most transformed host cells will express several copies of immunoglobulin heavy and light chains from the diverse library, and will express chimeric antibodies (antibodies encoded by all or part of two or more genes) (Nisonoff, A., et al., *In The Antibody Molecule*, Academic Press, NY p. 238 (1975)). These chimeric antibodies are of two types: those in which one chain is encoded by a host cell gene and the other chain is encoded by an exogenously introduced antibody gene and those in which both the light and the heavy chain are encoded by an exogenous antibody gene. Both types of antibodies will be secreted. A library of cells producing antibodies of diverse specificities is produced as a result. The library of cells can be stored and maintained indefinitely by continuous culture and/or by freezing. A virtually unlimited number, of cells can be obtained by this process.

Isolation of Cells Producing Antigen-Binding Molecules of Selected Specificity

Cells producing antigen-binding molecules of selected specificity (i.e., which bind to a selected antigen) can be identified and isolated using nitrocellulose filter layering or known techniques. The same methods employed to identify and isolate hybridoma cells producing a desired antibody can be used: cells are pooled and the supernatants tested for reactivity with antigen (Harlow, E. and D. Lane, *Antibodies: A Laboratory Manual*, Cold Spring Harbor Laboratory, N.Y., p. 283 (1988). Subsequently, individual clones of cells are identified, using known techniques. A preferred method for identification and isolation of cells makes use of nitrocellulose filter overlays, which allow the screening of a large number of cells. Cells from the library of transfected myeloma cells are seeded in 10 cm$^2$ petri dishes in soft agar (Cook, W. D. and M. D. Scharff, *PNAS*, 74:5687 (1977); Paige, C. J. et al., *Methods in Enzymol.*, 150:257 (1987)) at a density of $10^4$ colony forming units, and allowed to form small colonies (approximately 300 cells). A large number of dishes (>100) may be so seeded. Cells are then overlayed with a thin film of agarose (<1 mm) and the agarose is allowed to harden. The agarose contains culture medium without serum. Nitrocellulose filters (or other protein-binding filters) are layered on top of the agarose, and the dishes are incubated over night. During this time, antibodies secreted by the cells will diffuse through the agarose and adhere to the nitrocellulose filters. The nitrocellulose filters are keyed to the underlying plate and removed for processing.

The method for processing nitrocellulose filters is identical to the methods used for Western blotting (Harlow, E. and D. Lane, *Antibodies: Laboratory Manual*, Cold Spring Harbor, N.Y., p. 283 (1988)). The antibody molecules are adsorbed to the nitrocellulose filter. The filters, as prepared above, are then blocked. The desired antigen, for example, keyhole lymphet hemocyanin (KLH), which has been iodinated with radioactive $^{125}$I, is then applied in Western blotting buffers to the filters. (Other, non radiographic methods can be used for detection). After incubation, the filters are washed and dried and used to expose autoradiography film according to standard procedures. Where the filters have adsorbed antibody molecules which are capable of binding KLH, the autoradiography film will be exposed. Cells expressing the KLH reactive antibody can be identified by determining the location on the dish corresponding to an exposed filter; cells identified in this manner can be isolated using known techniques. Cells which are isolated from a region of the dish can then be rescreened, to insure the isolation of the clone of antigen-binding molecule-producing cells.

Isolation of Genes Encoding Molecules of Selected Specificity and Purification of Encoded Antigen-Binding Molecules The gene(s) encoding an antigen-binding molecule of selected specificity can be isolated. This can be carried out, for example, as follows: primers D and C (see FIGS. 2 and 3) are used in a polymerase chain reaction, to produce all the heavy chain variable region genes introduced into the candidate host cell from the library. These genes are cloned again in the framework vector pFHC at the RE1 and RE2 sites. Similarly, all the light chain regions introduced into the host cell from the library are cloned into the light chain vector, pFLC. Members of the family of vectors so obtained are then transformed pairwise into myeloma cells, which are tested for the ability to produce and secrete the antibody with the desired selectivity. Purification of the antibody from these cells can then be accomplished using standard procedures (Johnstone, A. and R. Thorpe, *Immunochem. in Practice*, Blackwell Scientific, Oxford, p. 27 (1982); Harlow, E. and D. Lane, *Antibodies: A Laboratory Manual*, Cold Spring Harbor Laboratory N.Y., p. 283 (1998)).

Alteration of Affinity Cell of Antigen-Binding Molecules

It is also possible to produce antigen-binding molecules whose affinity for a selected antigen is altered (e.g., different from the affinity of a corresponding antigen-binding molecule produced by the present method). This can be carried out, for example to increase the affinity of an antigen-binding molecule by randomly mutagenizing, the genes isolated as described above using previously-described mutagenesis methods. Alternatively, the variable region of antigen-binding molecule-encoding genes can be sequenced and site directed mutagenesis performed to mutate the complementarity determining regions (CDR) (Kabat, E. A. *J. Immunol.*, 141:S 25–36 (1988)). Both processes result in production of a sublibrary of genes which can be screened for antigen binding molecules of higher affinity or of altered affinity after the genes are expressed in myeloma cells.

Alternative Materials and Procedures for Use in the Present Method

In addition to those described above for use in the method of the present invention, other materials (e.g., starting materials, primers) and procedures can be used in carrying out the method. For example, use of PCR technology to clone a large collection of cDNA genes encoding variable regions-of heavy chains has been described above. Although primers from the $C\mu$ class were described as being used in unidirectional nested PCR, the present invention is not limited to these conditions. For example, primers from any of the other heavy chain classes $C\gamma_3$, $C\gamma_1$, $C\gamma_{2b}$, $C\alpha$ for example) or from light chains can be used. $C\mu$ was described as of particular use because of the fact that the entire repertoire of heavy chain variable regions are initially expressed as IgM. Only following heavy chain class switching are these variable regions expressed with a heavy chain of a different class (Shimizu, A. and T. Honjo, *Cell*, 36:801–803 (1984)). In addition, the predominant population of B cells in nonimmune spleen cells is IgM$^+$cells (Cooper, M. D. and P. Burrows, *In Immunoglobulin Genes*, Academic Press, N.Y. p. 1 (1989)). Although unidirectional nested PCR amplification is described above, other PCR procedures, as well as other DNA amplification techniques can be used to amplify DNA as needed in the present invention. For example, bidirectional PCR amplification of antibody variable regions can be carried out. This approach requires use of multiple degenerate 5' primers (Orlandi, R., et al., *Proc. Natl. Acad. Sci. USA*, 86:3833 (1989); Sastry, L., et L., *Proc. Natl. Acad. Sci, USA*, 86:5728 (1989)). Bidirectional amplification may not pick up the same full diversity of genes as can be expected from unidirectional PCR.

In addition, methods of introducing further diversity into the antibody library other than the method for random mutagenesis utilizing PCR described above can be used. Other methods of random mutagenesis, such as that described by Sambrook, et al., (Sambrook, J., et al., *Molecular Cloning: A Laboratory*, Cold Spring Harbor Laboratory Press, Cold Spring Harbor, N.Y. (1989)) can be used, as can direct mutagenesis of the complementarity determining regions (CDRs).

Framework vectors other than one using a mouse $C\mu$ heavy chain constant region, which contains the $C\mu$ enhancer and introns and a viral promoter (described previously) can be used for inserting the products of PCR. The vectors described were chosen for their subsequent use in the expression of the antibody genes, but any eukaryotic or prokaryotic cloning vector could be used to create a library of diverse cDNA genes encoding variable regions of antibody molecules. The inserts from this vector could be transferred to any number of expression vectors. For example, other framework vectors which include intronless genes can be constructed, as can other heavy chain constant regions. In addition to plasmid vectors viral vectors or retroviral vectors can be used to introduce genes into myeloma cells.

The source for antibody molecule mRNAs can also be varied. Purified resting B lymphocytes from mouse nonimmunized spleen are described above as such a source. However, total spleens immunized or not) from other animals, including humans, can be used, as can any source of antibody-producing cells (e.g., peripheral blood, lymph nodes, inflammatory tissue, bone marrow).

Introduction of H and L chain gene DNA into myeloma cells using cotransformation by electroporation or protoplast fusion methods is described above (Morrison, S. L., and V. T. Oi, *Adv. Immunol.*, 44:65 (1989)). However, any means by which DNA can be introduced into living cells in vivo can be used, provided that it does not significantly interfere with the ability of the transformed cells to express the introduced DNA. In fact, a method other than cotransformation, can be used. Cotransfection was chosen for its simplicity, and because both the H and L chains can be introduced into myeloma cells. It may be possible to introduce only the H chain into myeloma cells. Moreover, the H chain itself in many cases carries sufficient binding affinity for antigen. However, other methods can also be used. For example, retroviral infection may be used. Replication-incompetent retroviral vectors can be readily constructed which can be packaged into infective particles by helper cells (Mann, R., et al., *Cell*, 33:153–159 (1903)). Viral titers of $10^5$ infectious units per ml. can be achieved, making possible the transfer of very large numbers of genes, into myeloma cells.

Further increases in the diversity of antibody-producing cells than results from the method described above can be generated if light and heavy chain genes are introduced separately into myeloma cells. Light chain genes can be introduced into one set of myeloma cells with one selectable marker, and heavy chains into another set of cells with a different selectable marker. Myeloma cells containing and expressing both H and L chains could then be generated by the highly efficient process of polyethylene glycol mediated cell fusion (Pontecorvo, G., *Somatic Cell Genetics*, 1:397 (1975)). Thus, a method of screening diverse libraries of antibody genes using animal cells is not limited by the number of cells which can be generated, but by the number of cells which can be screened.

Methods of identifying antigen-binding molecule-expressing cells expressing an antigen-binding molecule of selected specificity other than the nitrocellulose filter overlay technique described above can be used. An important characteristic of any method is that it be useful to screen large numbers of different antibodies. With the nitrocellulose filter overlay technique, for example, if 300 dishes are prepared and $10^4$ independent transformed host cells per dish are screened, and if, on average, each cell produces ten different antibody molecules, then 300×$10^4$×3, or about $10^7$ different antibodies can be screened at once. However, if the antibody molecules can be displayed on the cell surface, still larger numbers of tills can be screened using affinity matrices to pre-enrich for antigen-binding cells. There are immortal B cell lines, such as $BCL_1B_1$, which will express IgM both on the cell surface and as a secreted form (Granowicz, E. S., et al., *J. Immunol.*, 125:976 (1980)). If such cells are infected by retroviral vectors containing the terminal C$\mu$ exons, the infected cells will likely produce both secreted and membrane bond forms of IgM (Webb, C. F. et al. *J. Immunol.*, 143:3934–3939 (1989)). Still other methods can be used to detect antibody production. If the host cell is *E. coli* a nitrocellulose overlay is possible, and such methods have been frequently used to detect *E. coli* producing particular proteins (Sambrook, J., et al., *Molecular Cloning: A Laboratory Manual*, Cold Spring Harbor Laboratory Press, Cold Spring Harbor, N.Y. (1989)). Other methods of detection are possible and one in particular, which involves the concept of "viral coating", is discussed below.

Viral coating can be used as a means of identifying viruses encoding antigen-combining molecules. In this method, a viral vector is used to direct the synthesis of diverse antibody molecules. Upon lytic infection of host cells, and subsequent cell lysis, the virus becomes "coated" with the antibody product it directs. That is, the antibody molecule becomes physically linked to the outside of a mature virus particle, which can direct its synthesis. Methods for viral coating are described below. Viruses coated by antibody can be physically selected on the basis of their affinity to antigen which is attached to a solid support. The number of particles which can be screened using this approach is well in excess of $10^9$ and it is possible that $10^{11}$ different antibody genes could be screened in this manner. In one embodiment, an affinity matrix containing antigen used to purify those viruses encoding antibody molecules with affinity to antigen and which coat the surface of the virus which encodes those antibodies is used.

One method of viral coating is as follows: A diverse library of bacteriophage λ encoding parts of antibody molecules that are expressed in infected *E. coli* and which retain the ability to bind antigens is created. using known techniques (Orlandi, R., et al., *Proc. Natl. Acad. Sci. USA*, 86:3833 (1989); Huse, W. D. et al., *Science*, 246:1275 (1989); Better, H., et al., *Science*, 240:1041 (1988); Skerra, A. and A. Pluckthon *Science*, 240:1038 (1988)). Bacteria infected with phage are embedded in a thin film of semisolid agar. Greater than $10^7$ infected bacteria may be plated in the presence of an excess of uninfected bacteria in a volume of 1 ml of agar and spread over a 10 $cm^2$ surface. The agar contains monovalent antibody "A" (Parham, P., *In Handbook of Experimental Immunology: Immunochem.*, Blackwell Scientific Publishers, Cambridge, Mass., pp. 14.1–14.23 (1986)), which can bind the λ coat proteins and which has been chemically coupled to monovalent antibody "B", which can bind an epitope on all viral directed antibody molecules. Monovalent antibodies are used to prevent the crosslinking of viral particles. Upon lytic burst, progeny phage particles become effectively cross linked to the antibody molecule they encode. Because lysis occurs in semisolid medium, in which diffusion is slow, cross linking between a given phage and the antibody encoded by another phage is minimized. A nitrocellulose filter (or other protein binding filter) is prepared as an affinity matrix by adsorbing the desired antigen. The filter is then blocked so that no other proteins bind nonspecifically. The fitter is overlayed upon the agar, and coated phage are alloyed to bind to the antigen by way of their adherent antibody molecules. Filters are washed to remove nonspecifically bound phage. Specifically bound phage therefore represent phage encoding antibodies with the desired specificity. These can now be propagated by reinfection of bacteria.

Thus the present invention makes it possible to produce antigen-binding molecules which, like antibodies produced by presently-available techniques, bind to a selected antigen (i.e., having binding specificity). Antibodies produced as described can be used, for example, to detect and neutralize antigens and deliver molecules to antigenic sites.

EXAMPLE I

Amplification of IgM Heavy Chain Variable Region DNA from mRNA

IgM heavy chain variable DNA is amplified from mRNA by the procedure represented schematically in FIG. 2. In FIG. 2, Panel A depicts the relevant regions of the poly adenylated mRNA encoding the secreted form of the IgM heavy chain. In Panel A, S denotes the sequences encoding the signal peptide which causes the nascent peptide to cross the plasma membrane, a necessary step in the processing and secretion of the antibody. V, D and J derive from separate exons and together comprise the variable region. $C_H1$, $C_H2$, and $C_H3$ are the three constant domains of C$\mu$. "Hinge" encodes the hinge region. C. B and Z are oligonucleotide PCR primers used in the amplification process. The only constraints on Primers B and Z are that they are complementary to the mRNA, and occur in the order shown relative to C. Primer C, in addition to being complementary to mRNA, has an extra bit of sequence at its 5' end which allows the cloning of its PCR product. This is described below. Panel B depicts the reverse transcript DNA product of the mRNA primed by oligonucleotide Z, with the addition of poly-dC by terminal transferase at the 3' end of the product. Panel C depicts the annealing of primer A to the reverse transcript DNA represented in Panel B. Primer A contains the restriction endonuclease site RE1, with additional DNA at its 5' end. The constraints on the RE1 site are described in Example 2. Panel D depicts the final double stranded DNA PCR product made utilizing primers A and B. Panel E depicts the PCR product shown in Panel D annealed to Primer C. Panel F is al blow up of panel E showing the structure of primer C. Primer C consists of two parts; a 3' part complementary to IgM heavy chain mRNA as shown, and a 5' part which contains restriction site RE2 and spacer. Constraints on RE2 are described in Example 2. Panel G depicts the final double stranded DNA PCR product utilizing Primers A and C and the product of the previous PCR (depicted in Panel D) as template. The S, V, D, J regions are again depicted.

EXAMPLE 2

Construction of Heavy Chain Framework Vector pFHC

A heavy chain framework vector, designated pFHC, is constructed, using known techniques (See FIG. 3). It is useful for introducing antibody-encoding DNA into host cells, in which the DNA is expressed resulting in antibody production. The circular plasmid (above) is depicted linearized (below) and its relevant components are shown. The neomycin antibiotic resistance gene (neo$^R$) is useful for selecting transformed animal cells (Sambrook, J., et al., *Molecular Cloning: A laboratory Manual*, 2d Ed., Cold Sprint Harbor Laboratory Press, Cold Spring Harbor, N.Y. (1989)). The bacterial replication origin and ampicillin antibiotic resistance genes, useful respectively, for replication in *E. coli* and rendering *E. coli* resistant to ampicillin, can derive from any number of bacterial plasmids, including PBR322 (Sambrook, J., et al., *Molecular Cloning: A Laboratory Manual*, 2d Ed., Cold Spring Harbor Laboratory Press, Cold Spring Harbor, N.Y. (1989)). The Cμ enhancer, which derives from the intron between exons J and $C_H^1$ of the Cμ gene, derives from any one of the cloned Cμ genes (Kawakami, T., et al., *Nucleic Acids Research*, 8:3933 (1980); Honjo, T., *Ann. Rev. Immunol.*, 1:499 (1983)) and increases levels of transcription from antibody genes. LTR contains the viral promoter from the Moloney MLV retrovirus DINA (Mulligan, R. C. *Experimental Manipulation of Gene Expression*, New York Academic Press, p. 155 (1983)). D represents the PCR primer described in the text, depicted in its 5' to 3' orientation. The only constraints on D are its orientation, its complementarity to pFHC and its order relative to the RE1 and RE2 cloning sites. Preferably, D is within 100 nucleotides of RE1. The cDNA cloning site contains restriction endonuclease sites RE1 and RE2, separated by spacer DNA which allows their efficient cleavage. The constraints on RE1 and RE2 are described below. The Cμ exons, as described in the text and literature, direct the synthesis of IgM heavy chain. Only part of $C_H1$ is present, as described below. $C_H3$ is chosen to contain the Cμs region which specifies a secreted form of the Heavy chain ((Kawakami, T., et al., *Nucleic Acids Research*, 8:3933 (1980); Honjo, T., *Ann. Rev. Immunol.*, 1:499 (1983)). Finally, pFHC contains poly A addition and termination sequences which can be derived from the Cμ gene itself (Honjo, T., *Ann. Rev. Immunol.*, 1:499 (1983); Kawakami, T., et al., *Nucleic Acids Research*, 8:3933 (1980)). One potential advantage of using the entire Cμ gene is that in some host cell systems, a membrane bound and secreted form of IgM may be expressed (Granowicz, E. S., et al., *J. Immunol*, 125:976 (1980)).

The plasmid can be produced by combining the individual components, or nucleic acid segments, depicted in FIG. 3, using PCR cassette assembly (See below). Because the entire nucleotide sequence of each component is defined, the entire nucleotide sequence of the plasma is defined.

The constraints on RE1 are simple. It should be the sole cleavage site on the plasmid for its restriction endonuclease. The choice of RE1 can be made by computer based sequence analysis (Intelligenetics Suite, Release 5:35, Intelligenetics).

The constraints on RE2 are more complex. First, it must be the sole cleavage site on the plasmid for its restriction endonuclease, as described for RE1. Moreover, the RE2 site must be such that when the PCR product is inserted, a gene is thereby created which is capable of directing the synthesis of a complete IgM heavy chain. This limits the choices for RE2, but the choices available can be determined by computer based sequence analysis. The choices can be determined as follows. First, a list of restriction endonucleases that do not cleave pFHC is compiled (see Table 1).

TABLE 1

Non-Cutting Enzymes for the Mouse Cμ Gene

| AatII | AhaII | AseI |
|---|---|---|
| AvrII | BgII | BspHI |
| BssMII | BstBI | ClaI |
| DraI | EagI | EcoRI |
| EcoRV | FspI | HgaI |
| HincII | HpaI | KpnI |
| MluI | NaeI | NarI |
| NdeI | NotI | NruI |
| PaeR7I | PvuI | RsrII |
| SacII | SalI | ScaI |
| SfII | SnaBI | SpeI |
| SphI | SspI | StuI |
| Tth111I | XbaI | XhoI |

These are called the "rare non-cutters." Next, the sequence of $C_H1$ is rewritten with "N" at the third position of each codon and entered into the computer. This is called the "N-doped sequence" (See FIG. 4). Next, the rare non-cutters are surveyed by computer analysis for those which will cleave the N-doped sequence. The search program will show a possible restriction endonuclease site assuming a match between N and the restriction endonuclease cutting site. For example, with 39 rare non-cutters, 22 will cleave the N-doped sequence of Cμ $C_H1$, many of them several times (see Table 2). In this table, "Def" means a definite cut site, of which there are none, because of the Ns. "Pos" means a possible cleavage site at the indicated nucleotide position if N is chosen appropriately. "Y" indicates any pyrimidine, "R" indicates any purine and "N" indicates any nucleotide. The nucleotide positions refer to coordinates represented in FIG. 4.

TABLE 2

| ENZYME | RECOGNITION | CUT SITE |
|---|---|---|
| AatII | (GACGTC) | Def:none |
| | | Pos:250 309 |
| AhaII | (GRCGYC) | Def:none |
| | | Pos:247 306 |
| AvrII | (CCTAGG) | Def:none |
| | | Pos:204 |
| BspHI | (TCATGA) | Def:none |
| | | Pos:138 |
| BsshII | (GCGCGC) | Def:none |
| | | Pos:189 |
| EcoRI | (GAATTC) | Def:none |
| | | Pos:195 334 |
| EcoRV | (GATATC) | Def:none |
| | | Pos:214 |
| HgaI | (GACGCNNNNN) | Def:none |
| | (NNNNNNNNNNNGCGTC) | Pos:284 |
| HincII | (GTYRAC) | Def:none |
| | | Pos:183 220 |
| HpaI | (GTTAAC) | Def:none |
| | | Pos:220 |
| KpnI | (GGTACC) | Def:none |
| | | Pos:408 |
| NruI | (TCGCGA) | Def:none |
| | | Pos:174 193 303 |
| PaeR7 | (CTCGAG) | Def:none |
| | | Pos:190 339 |
| PvuI | (CGATCG) | Def:none |
| | | Pos:178 |
| ScaI | (AGTACT) | Def:none |
| | | Pos:209 266 284 |
| SpeI | (ACTAGT) | Def:none |
| | | Pos:131 167 359 |
| SphI | (GCATGC) | Def:none |
| | | Pos:338 |

TABLE 2-continued

| ENZYME | RECOGNITION | CUT SITE |
|---|---|---|
| SspI | (AATATT) | Def:none |
| | | Pos:371 |
| StuI | (AGGCCT) | Def:none |
| | | Pos:149 |
| Tth111I | (GACNNNGTC) | Def:none |
| | | Pos:212 |
| XbaI | (TCTAGA) | Def:none |
| | | Pos:338 |
| XhoI | (CTCGAG) | Def:none |
| | | Pos:190 339 |

Most of these cleavage sites (about 60%) are compatible with the amino acids specified by $C_H1$. Therefore, it is possible to mutate $C_H1$ to create a unique site for such an enzyme without altering the amino acid sequence incoded by $C_H1$. One sequence which illustrates this is shown below:

```
1) . . . ala met gly cys leu ala arg asp . . .

2) . . . GCC ATG GGC TGC CTA GCC CGG GAC . . .

3) . . . GCC ATG GGC TGC GTA GCG CGC GAC . . .
                            ---------
                              BssHII
```

Line 1 represents part of the actual amino acid sequence specified by the mouse $C\mu$ $C_H1$ gene region, and line 2 is the actual nucleotide sequence. By changing the sequence to the indicated nucleotides underlined on line 3, a, cleavage site for the rare non-cutter BssHII is created. The new sequence (containing the BssHII site) GCG CGC still encodes the identical amino acid sequence. Therefore, the sequence of the primer C is chosen to be the complement of line 3, and RE2 is the BssHII site. Such a primer will function in the PCR and vector construction as desired. Other examples are possible, and the same process can be used in designing vectors and primers for cloning light chain variable regions.

The choice for primer C puts a constraint on pFHC. In the example shown, the $C_H1$ region contained-on pFHC must begin at its 5' end with the mutant sequence GCG CGC. Such mutant fragments can be readily made by the process of PCR cassette assembly described below.

The process of PCR cassette assembly is a method of constructing plasmid molecules (in this case the plasmid pFHC) from fragments of DNA of known nucleotide sequence. One first compiles a list of restriction endonucleases that do not cleave any of the fragments. Each fragment is then individually PCR amplified using synthesized oligonucleotide primers complementary to the terminal sequences of the fragment. These primers are synthesized to contain on their 5' ends restriction endonuclease cleavage sites from the compiled list. Thus, each PCR product can be so designed that each fragment can be assembled one by one into a larger plasmid structure by cleavage and ligation and transformation into $E.$ $coli$. Using this method, it is also possible to make minor modifications to the terminal sequence of the fragment being amplified. This is done by altering the PCR primer slightly so that a mismatch occurs. In this way it is possible to amplify the $C\mu$ gene starting precisely from the desired point in $C_H1$ (as determined by oligo C above) and creating the RE2 endonuclease cleavage site.

EQUIVALENTS

Those skilled in the art will recognize, or be able to ascertain using no more, than routine experimentation, many equivalents to the specific embodiments of the invention described specifically herein. Such equivalents are intended to be encompassed in the scope of the following claims.

What is claimed is:

1. An in vitro process for synthesizing DNA encoding a family of antigen-combining proteins, comprising the steps of:
   (a) obtaining DNA containing genes encoding antigen-combining proteins;
   (b) combining the DNA containing genes encoding antigen-combining proteins with sequence specific primers which are oligonucleotides homologous to conserved regions of the genes; and
   (c) performing sequence specific gene amplification.

2. The process of claim 1 wherein sequence specific gene amplification is performed by the polymerase chain reaction.

3. The process of claim 2 wherein the sequence specific primers are bidirectional.

4. The process of claim 3 wherein the sequence specific primers are nested unidirectional primers.

5. The process of claim 1 wherein the antigen-combining proteins are immunoglobulins.

6. The process of claim 5 wherein the immunoglobulins are selected from the group consisting of heavy chains and light chains.

7. The process of claim 7 wherein the heavy chains are $\mu$ chains.

8. The process of claim 1 wherein the DNA containing genes encoding antigen-combining proteins is cDNA of RNA from antibody-producing cells.

9. The process of claim 1 wherein the DNA containing genes encoding antigen-combining proteins is genomic DNA from antibody-producing cells.

10. The process of claim 7 wherein the antigen-combining proteins are of mammalian origin.

11. The process of claim 1 wherein the primers are oligonucleotides homologous to conserved regions of the constant regions of immunoglobulin genes.

12. The process of claim 1 wherein the primers are oligonucleotides homologous to the conserved regions of the variable regions of immunoglobulin genes.

13. The process of claim 1 wherein the primers contain at least one restriction endonuclease cloning site.

14. The method of claim 1, comprising cloning the amplified genes into a vector.

15. The method of claim 14 wherein the vector is a prokaryotic vector or a eukaryotic vector.

16. The method of claim 14 wherein the vector is a viral vector or a retroviral vector.

17. The method of claim 14 wherein the vector is a plasmid.

18. The method of claim 14 wherein the pFHC plasmid or the pLHC plasmid.

19. The method of claim 14 wherein the vector is selected from the group consisting of expression vectors and cloning vectors.

20. The method of claim 19 wherein the expression vector is appropriate for expression of the variable region of an antigen-combining protein as a chimeric molecule in register with a framework protein.

21. The method of claim 20 wherein the framework protein is an immunoglobulin.

22. The method of claim 21 wherein the immunoglobulin is all or a portion of the constant region of the $\mu$ heavy chain.

23. The method of claim 16 further comprising creating a collection of viral particles from viral vector-based libraries of DNA encoding antigen-combining proteins by the process of introducing viral vectors into host cells in which they replicate and form viral particles.

\* \* \* \* \*